Patented Dec. 26, 1939

Plant Pat. 351

UNITED STATES PATENT OFFICE

351

PEACH TREE

Vine Carson Campbell, Yakima County, Wash., assignor to Walter Dibble Plough, Wenatchee, Wash.

No Drawing. Application April 10, 1939, Serial No. 267,141

1 Claim. (Cl. 47—62)

The present discovery is an improvement over the Rochester variety and the improvement pertains particularly to an earlier date of ripening.

Some years ago I planted in my orchard near Yakima, about a dozen Rochester peach pits, expecting to bud these over to apricots. These were budded the following summer but one of the buds failed to grow and the tree grew up as a peach seedling. I did not disturb this tree and when it came into bearing I noticed that the fruit appeared to be identical with that of the Rochester trees which were growing only a few feet away, but that it ripened about three weeks earlier. I did not think much about this at the time, supposing it might be due to the fact that this was a young tree, or to some other such cause. However, the next year the tree again bore fruit which again ripened about three weeks earlier than that on the Rochester trees. I then decided that this seedling tree had produced a new variety, and from that time on I watched it carefully.

I planted out some peach pits and budded these to the new seedling peach. Six of these trees have since borne fruit and the time of ripening was the same as that of the original seedling.

The tree and fruit of this new variety seem to be identical with Rochester, except as to the time of ripening which is about three weeks earlier than that of Rochester. In this climate both varieties are semi-clingstone, but each when fully ripened is nearly and sometimes completely free.

Following is a detailed description of my new variety of peach.

Tree:

*Growth.*—Vigorous; upright-spreading; productive.

*Size.*—Large.

*Leaves.*—Size—six inches long, 1½ inches wide. Shape—ovate-lanceolate; margin shallowly crenate. Texture—thin; leathery. Petiole—one-half inch long; heavy.

Flowers:

Early.

*Color.*—Pale pink.

*Size.*—One inch in diameter.

Fruit:

Early, July 1st to 15th.

*Size.*—2¾ to 3¼ inches in diameter.

*Shape.*—Round - oblate, compressed, often bulged near the apex; cavity wide, deep-flaring; suture shallow; apex variable.

*Color.*—Orange-yellow, blushed with deep, dark red, mottled.

*Pubescence.*—Heavy.

*Skin.*—Thick; tough; separates from pulp.

*Flesh.*—Yellow, stained with red near the pit; juicy; tender; sweet; highly flavored; sprightly; very good quality.

*Stone.*—Semi-cling; when fully ripened nearly (and sometimes completely) free. Shape—oval; plump; flattened near base. Surface—roughened, marked by large deep pits and short grooves.

Having thus disclosed my discovery, I claim:

A new and distinct variety of peach tree substantially as described, having the appearance and qualities of the Rochester variety except that it produces ripened fruit from eighteen to twenty-one days earlier.

VINE CARSON CAMPBELL.